(12) United States Patent
Langley et al.

(10) Patent No.: US 9,339,607 B2
(45) Date of Patent: May 17, 2016

(54) MEDICAMENT DELIVERY DEVICES

(75) Inventors: Christopher Nigel Langley, Warwickshire (GB); Christopher John Jones, Cloucestershire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 1178 days.

(21) Appl. No.: 13/254,580

(22) PCT Filed: Mar. 24, 2010

(86) PCT No.: PCT/EP2010/053811
§ 371 (c)(1),
(2), (4) Date: Mar. 15, 2012

(87) PCT Pub. No.: WO2010/112376
PCT Pub. Date: Oct. 7, 2010

(65) Prior Publication Data
US 2012/0179112 A1    Jul. 12, 2012

(30) Foreign Application Priority Data

Mar. 31, 2009 (EP) .................................... 09004648

(51) Int. Cl.
*A61M 5/315* (2006.01)
*A61M 5/142* (2006.01)
*A61M 5/145* (2006.01)

(52) U.S. Cl.
CPC ....... *A61M 5/31511* (2013.01); *A61M 5/14244* (2013.01); *A61M 5/14566* (2013.01);
(Continued)

(58) Field of Classification Search
CPC .................. A61M 5/315; A61M 2005/31518; A61M 5/31511; A61M 5/31501; A61M 5/31543; A61M 5/14244; A61M 5/14566; A61M 2005/14268; A61M 2005/14573; A61M 2005/3152; A61M 2205/6027
USPC .......................................................... 604/228
See application file for complete search history.

(56) References Cited

U.S. PATENT DOCUMENTS 5,637,095 A    6/1997  Nason et al.
5,808,203 A *  9/1998  Nolan, Jr. .......... A61M 5/14546
                                                    604/67

(Continued)

FOREIGN PATENT DOCUMENTS

EP     1372762 B1   2/2007
WO     9700091 A1   1/1997
(Continued)

*Primary Examiner* — Emily Schmidt
*Assistant Examiner* — Lauren M Peng
(74) *Attorney, Agent, or Firm* — McDonnell Boehnen Hulbert & Berghoff LLP

(57) ABSTRACT

A medicament delivery device (1) comprises a housing (2) for holding a medicament cartridge (9), a piston rod (22, 24) and a drive (11, 20). The medicament cartridge (9) has a medicament outlet and a bung (13) moveable axially along the medicament cartridge for dispensing a medicament, the piston rod has a plunger (24) for moving the bung and a lead member (22) telescopically coupled to the plunger (24) that may be driven by the drive (11, 20) to extend or retract the piston rod (22, 24). Additionally, the device comprises a linkage (40) coupled between the plunger (24) and an anchorage (44) and a drive member (20) telescopically coupled to the lead member (22). The drive (11) is operative to rotate the drive member (20) to telescopically move the lead member relative to the drive member whereby the plunger is moved relative to the lead member by way of the linkage (40).

12 Claims, 5 Drawing Sheets

(52) U.S. Cl.
CPC ............... *A61M2005/14268* (2013.01); *A61M 2005/14573* (2013.01); *A61M 2005/3152* (2013.01); *A61M 2005/31518* (2013.01); *A61M 2205/6027* (2013.01)

(56) References Cited

U.S. PATENT DOCUMENTS

| | | | |
|---|---|---|---|
| 7,967,795 | B1 | 6/2011 | Cabiri |
| 8,257,319 | B2 * | 9/2012 | Plumptre .......... A61M 5/31525 604/211 |
| 2004/0092873 | A1 * | 5/2004 | Moberg .............. A61M 5/1456 604/131 |
| 2005/0192543 | A1 * | 9/2005 | Sibbitt .............. A61M 5/31511 604/218 |
| 2007/0129675 | A1 * | 6/2007 | Summerville ........ A61M 5/508 604/110 |
| 2009/0093792 | A1 | 4/2009 | Gross et al. |
| 2010/0249721 | A1 | 9/2010 | Guillermo et al. |

FOREIGN PATENT DOCUMENTS

| | | |
|---|---|---|
| WO | 02076538 A1 | 10/2002 |
| WO | 2006133111 A2 | 12/2006 |

* cited by examiner

MEDICAMENT DELIVERY DEVICES

CROSS REFERENCE TO RELATED APPLICATIONS

The present application is a 35 U.S.C. 371 National Application of PCT/EP2010/053811 filed Mar. 24, 2010, which claims priority to European Patent Application No. 09004648.3, filed Mar. 31, 2009, the entire contents of which are incorporated entirely herein by reference.

The present invention relates to medicament delivery devices for delivering medicine to the human or animal body and in particular, but not exclusively, to devices having a replaceable medicament cartridge. Such devices are commonly used by those with diabetes for the administration of insulin.

Medicament delivery devices are routinely used by persons without formal medical training, i.e. patients where self-management of their condition is increasingly common. These circumstances set a number of requirements for medicament delivery devices of this kind. The injector should be robust in construction, yet easy to use in terms of its operation by a user and the manipulation of the parts. In the case of those with diabetes, some users will be of impaired vision and may also be physically infirm. Devices that are too large or cumbersome may therefore prove difficult to use, particularly for someone with reduced dexterity.

In order to increase ease of use, some medicament delivery devices are semi-automated, incorporating means to assist the user during dose setting and administration. Such devices may use an energy storage means, for example a spring, or may utilise a motor to drive the piston rod of the device.

One example of a motor driven device is shown in U.S. Pat. No. 5,637,095, wherein a motor drives a flexible drive member via a tape-drive means. An inherent problem with devices of this kind are the difficulties in accurately driving the piston member due to the flexible drive members utilised and the additional strain on the motor to both drive and retract the piston rod. Additionally, the time taken to retract the piston rod from within the cartridge can be prohibitively long.

WO 02/076538 describes medicament delivery device with a flexible piston rod arrangement and incorporates a constant force spring.

It is a disadvantage that these devices require a flexible drive member to advance the bung of the piston rod. Devices that utilise this type of drive means are sometimes referred to as round-the-corner type devices. The flexible drive members utilised by these devices, although reducing the overall form factor of the device, are limited in that the drive member must have sufficient rigidity to push against the piston rod, whilst having enough flexibility to allow it to effectively pass around a corner. As such, the reduction in form factor is limited by the relative rigidity of the flexible member required to push against the bung of the medicament cartridge.

An alternative approach to reducing the form factor of a device is described in WO 97/00091. The distal part of the telescopic piston rod is connected to the elastomeric piston of the syringe, and is prevented from rotating by a number of bushings surrounding the telescopic piston rod. The bushing of the largest diameter needs to fit within the diameter of the syringe with the consequence that the telescopic piston is only suitable for a syringe of considerable size.

EP 1372762 describes an alternative approach that utilises a transmission means to act on the nested piston members and advance the piston rod. However, the devices disclosed are large and cumbersome to use due to the space required to move the dial means to set the required dose.

It is an aim of the present invention to alleviate at least some of the aforementioned disadvantages.

The term "medicament delivery device" according to instant invention shall mean a single-dose or multi-dose or pre-set dose or pre-defined, disposable or re-useable device designed to dispense a user selectable or pre-defined dose of a medicinal product, preferably multiple doses, e.g. insulin, growth hormones, low molecular weight heparins, and their analogues and/or derivatives etc. Said device may be of any shape, e.g. compact or pen-type. Dose delivery may be provided through a mechanical (optionally manual) or electrical drive mechanism or stored energy drive mechanism, such as a spring, etc. Dose selection may be provided through a manual mechanism or electronic mechanism. Additionally, said device may contain components designed to monitor physiological properties such as blood glucose levels, etc. Furthermore, the said device may comprise a needle or may be needle-free. In particular, the term "medicament delivery device" may refer to a needle-based device providing multiple doses having an electrical drive mechanism, which is designed for use by persons without formal medical training such as patients. Preferably, the drug delivery device is of the automated-type, i.e. an auto-injector.

The term "housing" according to instant invention shall preferably mean any exterior housing ("main housing", "body", "shell") or interior housing ("insert", "inner body") having a unidirectional axial coupling to prevent proximal movement of specific components. The housing may be designed to enable the safe, correct, and comfortable handling of the drug delivery device or any of its mechanism. Usually, it is designed to house, fix, protect, guide, and/or engage with any of the inner components of the drug delivery device (e.g., the drive mechanism, cartridge, plunger, piston rod) by limiting the exposure to contaminants, such as liquid, dust, dirt etc. In general, the housing may be unitary or a multipart component of tubular or non-tubular shape. Usually, the exterior housing serves to house a cartridge from which a number of doses of a medicinal product may by dispensed.

The term "motor" according to the instant invention shall preferably mean any motorised means for driving the gearing system and ultimately the input drive means. In the instant invention a d.c. motor is preferably utilised although alternative means for driving the gearing system or the drive means may also be incorporated into the device.

According to a first aspect of the invention, there is provided a medicament delivery device comprising: a housing for holding a medicament cartridge, the medicament cartridge having a medicament outlet and a bung moveable axially along the medicament cartridge for dispensing a medicament; a piston rod having a plunger for moving the bung, and a lead member telescopically coupled to the plunger; a drive for extending or retracting the piston rod; and a linkage coupled between the plunger and an anchorage characterised in that the medicament delivery device includes a drive member telescopically coupled to the lead member, wherein the drive is operative to rotate the drive member to telescopically move the lead member relative to the drive member whereby the plunger is moved relative to the lead member by way of the linkage.

In a preferred embodiment, the linkage is flexible and inextensible and may pass over a pulley system to increase the efficiency of the transferral of the drive to the movement of the piston rod via the lead member. The flexibility of the linkage allows it to pass over the pulley system and also allows it to be configured into a confined space within the medicament delivery device. An additional effect of this flexibility allows the ends of the linkage on either side of the pulley wheel to be positioned to allow for optimal efficiency of the pulley system, preferably such parallel to the piston rod. This also allows for a reduction in the size of the medicament delivery device.

In this embodiment, the pulley system is located on the lead member and is preferentially a rotatable pulley wheel. As the drive member rotates, the lead member telescopically extends towards the bung. Simultaneously, due to the coupling of the free ends of the linkage to the housing and the plunger, and the path of the linkage over the pulley system, the plunger also telescopically extends with respect to the lead member towards the bung of the medicament cartridge, whereupon it acts upon the bung to dispense the contained medicament. In other words, the lead member with associated pulley wheel can be viewed as forming part of a moveable pulley, whereupon movement of the lead member or pulley wheel causes associated movement to the free element of the pulley, the plunger, due to the fixed position of one end of the linkage with respect to the housing.

The piston rod may be optionally retracted to its initial position through the use of a restoring force that acts in a direction counter to the drive. This may be motor drive assisted. This allows the piston rod to be quickly and fully retracted, for example when the medicament cartridge is replaced. The restoring force is preferentially provided by one or more springs connected between the plunger and the housing and are optimally coiled or constant-force springs. In operation, the one or more springs are initially in a wound configuration (when the piston rod is in a retracted condition) and are unwound into an extended position by the drive force due to the axial movement of the plunger relative to the housing. The springs are configured to produce a substantially constant force over the retraction distance of a sufficient amount to cause retraction. The one or more springs may also provide an electrical connection to a sensor located on the end of the plunger for detecting contact between the plunger and the bung.

The drive acts upon a drive member supported by the housing and acts either directly or via a gearing arrangement. Due to the coupling between the housing and the drive member, the drive member is prevented from moving substantially longitudinally, but is free to rotate relative to the housing. The drive force is preferentially supplied by a motor coupled to the drive member.

The drive member and the lead member are preferentially telescopically coupled by complimentary screw threads, specifically an external screw thread on the drive member and an internal screw thread on the lead member, and the lead member and the plunger are telescopically coupled by a spline arrangement. The anchorage is coupled to any axially fixed point relative to the piston rod assembly. In a preferred embodiment, the anchorage is coupled to the housing.

The drive member and the piston rod may also be substantially axially aligned to allow the width of the medicament delivery device to be minimised.

The invention will now be described, by way of example only, with reference to the accompanying drawings, in which.

Figure 1:
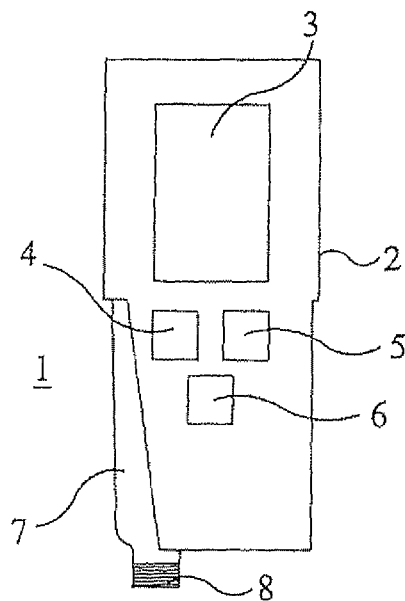
FIG. 1 is a front view of a medicament delivery device that may include an embodiment of the present invention.
Figure 2:
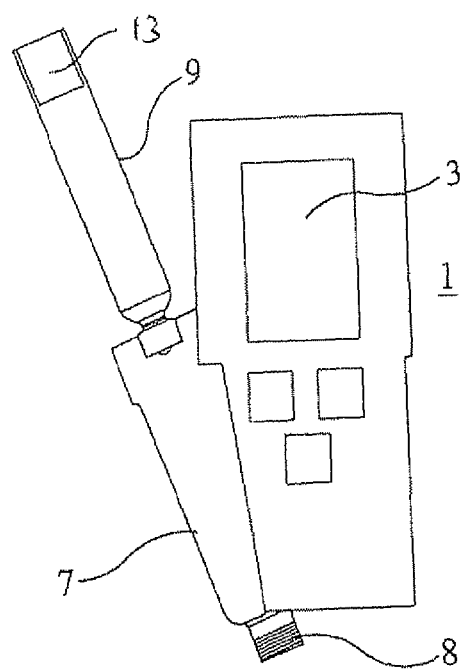
FIG. 2 is a front view of the medicament delivery device of FIG. 1 with a medicament cartridge door shown in an open position for receiving a medicament cartridge.

In FIG. 1, a medicament delivery device 1 comprises a case 2 having a display 3 for displaying functional information relating to the operation of the medicament delivery device, including the set dose and the number of doses remaining in the medicament cartridge. User interface buttons 4, 5 and 6 are provided to allow the user to operate the injector including priming, setting a dose, opening a medicament cartridge holder and door 7, and activating the dispensing of the set dose. A threaded needle hub 8 is provided to which a needle can be attached for dose delivery and subsequently removed and discarded. A cover (not shown) may be provided to fit over the lower portion of the case 2 to assist in protecting the device from the ingress of particles and fluid. FIG. 2 shows the medicament delivery device 1 with the cartridge holder and door 7 in an open position for receiving a replacement medicament cartridge 9.

Figure 3:
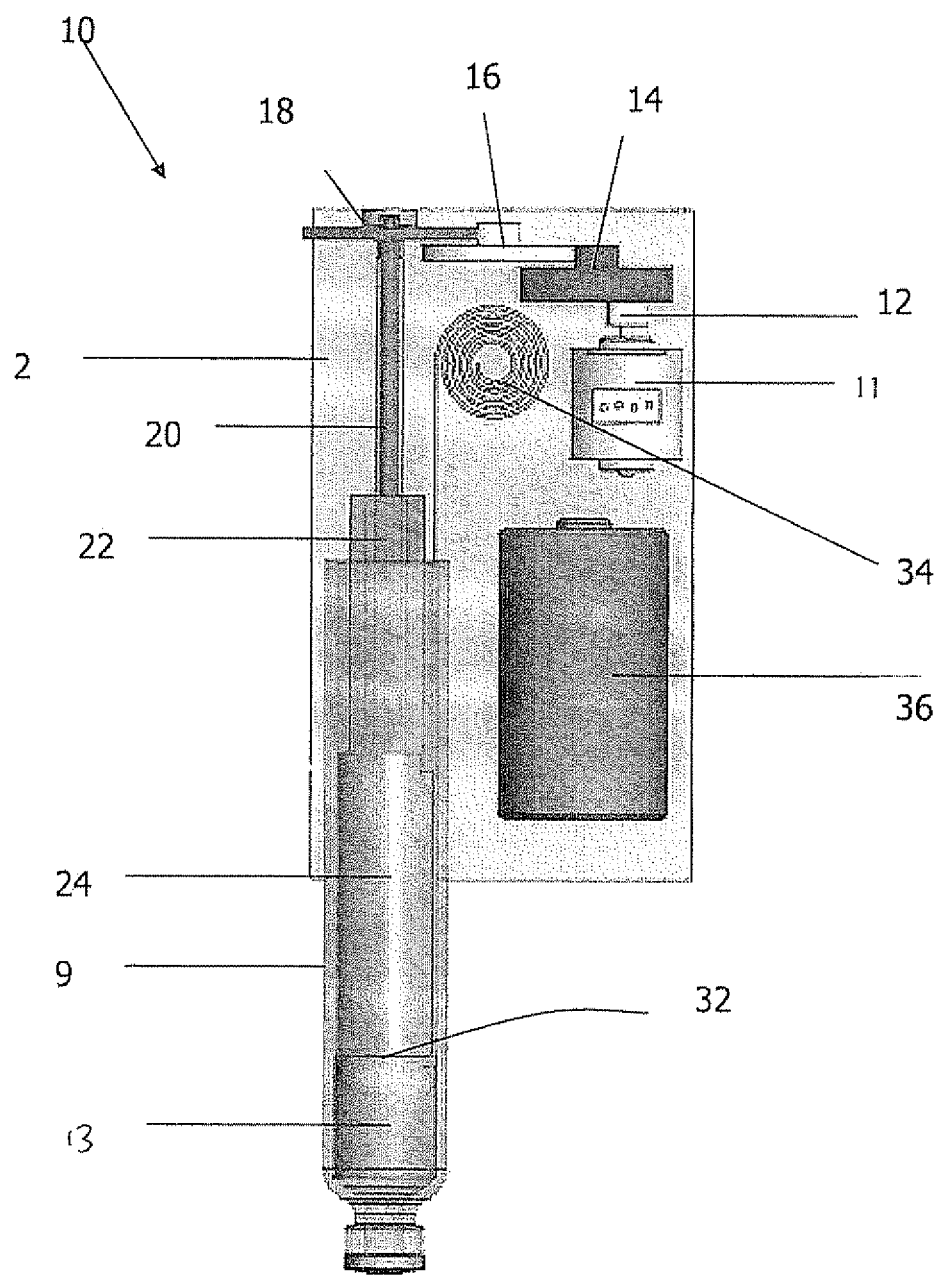
FIG. 3 is a plan view of a medicament delivery device including a piston rod and drive according to a first aspect of the present invention in which the piston rod is in an extended position.
Figure 4:
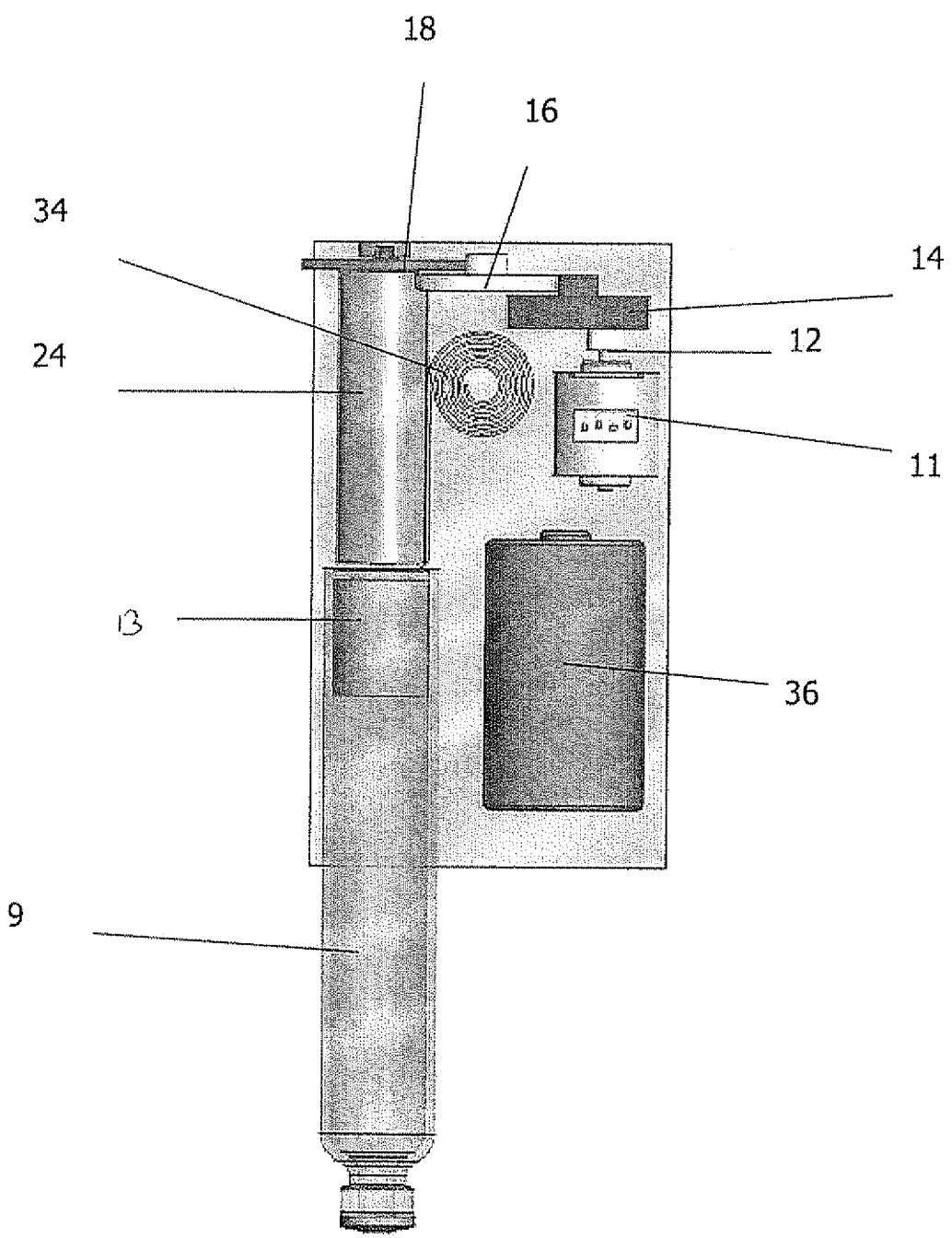
FIG. 4 is a plan view of the embodiment shown in FIG. 3 with the piston rod of the medicament delivery device in a fully retracted position.

FIGS. 3 and 4 show a cutaway of the medicament delivery device 1 shown generally at 10 wherein the housing 2 (shown in part only) and medicament cartridge 9 are shown in relation to the drive assembly. The medicament cartridge 9 comprises a bung 13 and is shown in partial ghost view to allow components within the cartridge to be seen.

Located within the housing 2 is a motor 11 is connected via a pinion gear 12 to a gear train comprising a first gear 14, a second gear 16 and a third gear 18.

A telescopically extendible piston rod 22, 24 comprising first and second piston members is also located within the housing. The first member may be considered to be a lead member 22 of the piston rod 22, 24 and the second member may be considered to be a plunger 24 that acts on the bung 13 of the medicament cartridge 9. Coupled to the lead member 22 is a rotatable drive member 20 to transmit the drive force from the motor 11 to the piston rod 22, 24. The drive member 20 is mounted for rotation with the third gear 18 and has an external helical thread 26 which engages with a corresponding internal thread 28 on the internal longitudinal surface of the lead member 22 (see FIG. 6). Due to the connection between the gear 18 and the drive member 20, the drive member 20 is axially fixed in position with respect to the gear train 14, 16, 18 and the housing 2; however it is free to rotate within the housing 2. It may be envisaged that the gear 18 and the drive member 20 form a single piece.

The external longitudinal surface of the lead member 22 is provided with a series of radially spaced longitudinally extending splines 30 which are adapted to engage in sliding engagement with a corresponding series of radially spaced longitudinally extending splines on the interior surface of the plunger 24. The plunger 24 terminates at its end remote from the lead member 22 in a pressure foot 32. The piston rod 22, 24 is rotationally fixed with respect to the housing by the engagement of ribs (not shown) on the lead member 22 that run on either side of a guide 25 (see FIG. 7). Additional end surfaces (not shown) may be provided only to allow the piston rod (22, 24) to be respectively disengaged in one direction.

A battery 36 provides a convenient power source for the motor 11 and the central control unit (not shown) of the injector.

The motor 11 may conveniently be controlled by a microprocessor (not shown) in response to user input.

Figure 5:
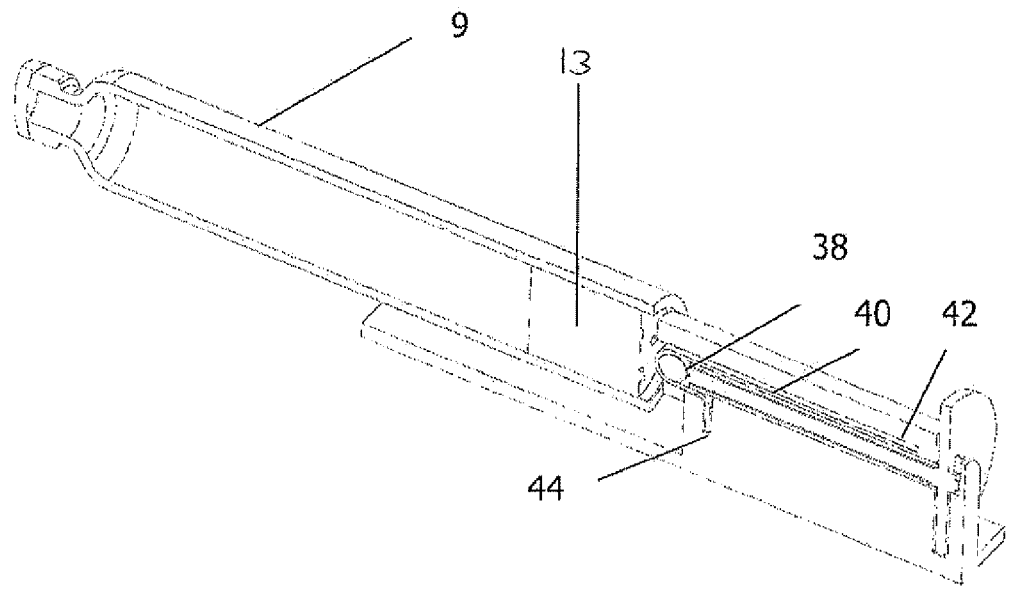
FIG. 5 is a perspective view in section of the embodiment shown in FIG. 3 with the piston rod in a fully retracted position.
Figure 6:
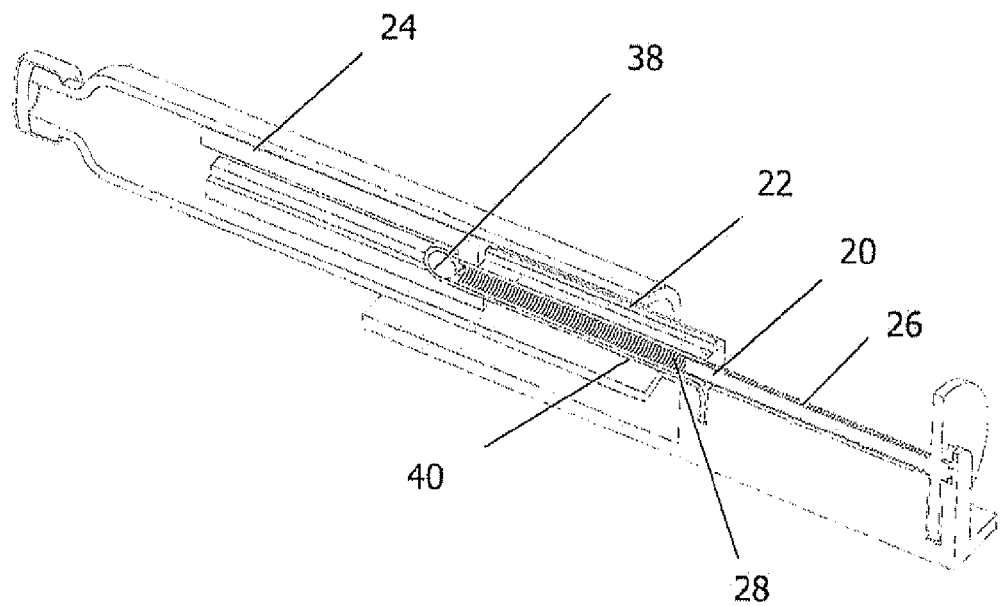
FIG. 6 is a perspective view in section of the embodiment shown in FIG. 3 with the piston rod in a fully extended position.

A cutaway view of the piston rod 22, 24 and the drive member 20 in a retracted and extended configuration is shown in FIGS. 5 and 6 (bung 13 not shown in FIG. 6) respectively. Additionally shown is a belt 40 provided with a first end 42 secured to the plunger 24 and a second end secured to the housing 2 at an anchorage point 44. The belt may be considered to be a linkage 40. The belt or linkage 40 is guided by a pulley wheel 38 and may be acted upon by the lead member 22 via the drive member 20. The belt 40 generally comprises a flexible, non-extensible elongate member.

In order to improve the efficiency of operating the belt 40, the pulley wheel 38 is mounted on the end of the lead member 22 remote from the drive member 20. The pulley wheel 38 is mounted for rotation about an axis perpendicular to the longitudinal axis of the piston rod 22, 24. In use, the pulley wheel 38 acts as a moveable pulley and provides a mechanical advantage, akin to a second class lever as it acts between the housing 2 and the plunger 24 via the belt 40.

Figure 7:
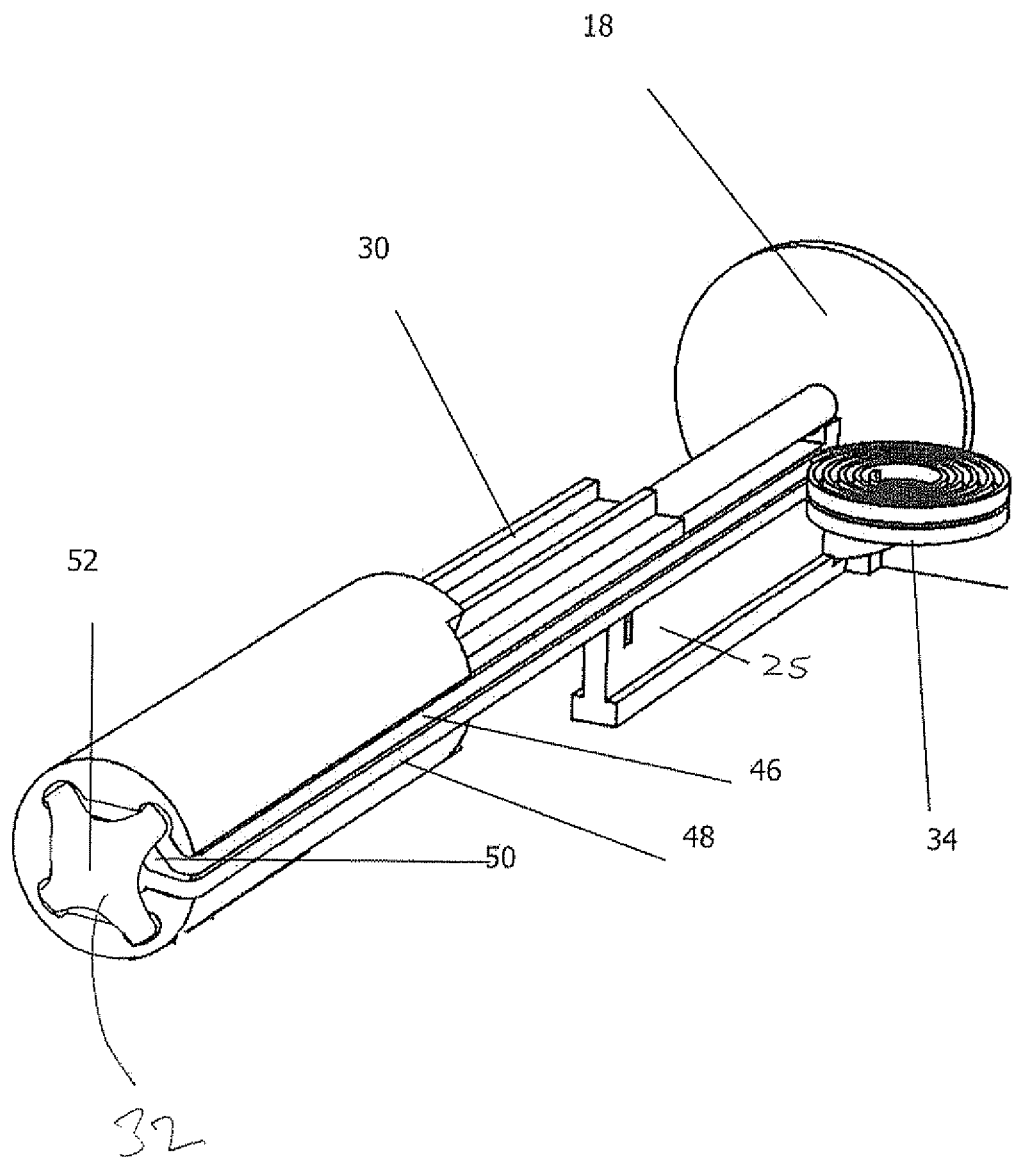
FIG. 7 is perspective view of the part arrangement shown in FIG. 3 with a detail of the retraction device.

FIG. 7 shows the piston rod 22, 24 and the drive member 20 assembly in an extended configuration. Mounted to the pressure foot 32 of the plunger 24 via its free end is a coiled spring support member 34 that is fixed to the housing 2 and is configured to receive one or more coiled steel springs 46, 48 that may be wound and unwound about the spring support member 34. The spring support member 34 may preferentially be made from a flexible plastic. Advantageously the springs are constant force springs, however it may be envisaged that alternative restoring means (for example differing spring means) may be utilised. The coiled steel springs 46, 48 are mounted on the flexible plastic support member 34 in a spaced arrangement with a gap 50 to provide electrical insulation between the springs 46, 48.

A dome switch 52 is mounted on pressure foot 32 at the end of the plunger 24. The arrangement of the coiled steel springs 46, 48 provide an electrical connection between the dome switch 52 and a central control unit (not shown) of the injector, when the switch is activated, allowing the potential provision of analysis or recognition means between the pressure foot 32 and the device control or display means (not shown).

On receipt of a suitable command, either from the user or via an automated process, the motor 11 is actuated to drive the gear train and so the drive member 20. On rotation of the drive member 20, the lead member 22 is driven outwardly in the direction of the bung by the engagement of the external helical thread 26 of the drive member 20 with the corresponding internal thread 28 on the internal longitudinal surface of the lead member 22. As the lead member 22 is driven outwardly, the pulley wheel 38 located on the lead member 22 presses against the belt 40. This movement of the pulley wheel 38 causes the belt 40 to pass over the pulley wheel 38. As one end of the belt 40 is fixed to the anchorage 44, only the end 42 connected to the plunger 24 is able to move via interaction with the plunger 24. Consequently, the belt 40 moves over the pulley 38 pulling the plunger 24 forwards towards the bung 13 of the medicament cartridge, drawing the plunger 24 from the retracted position shown in FIGS. 3 and 5 to the extended position shown in FIGS. 4 and 6. The radially spaced longitudinally extending splines 30 on the outer surface of the lead member 22 engage in sliding engagement with the corresponding series of radially spaced longitudinally extending splines on the interior surface of the plunger 24. The plunger 24 is thus driven towards the bung 13 until its pressure foot 32 contacts the bung 13. Further displacement of the plunger 24 displaces the bung 13 within the cartridge body 9 to cause the contained medicament to be expelled through a needle hub 8.

As the plunger 24 is displaced axially towards the bung 13 of the medicament cartridge 9 the coiled steel springs 46, 48 are uncoiled from their relaxed positions to tensed positions. The coiled steel springs 46, 48 can thereby ensure the linkage is in tension. Thus, when it is desired to retract the piston rod 22, 24, the motor 11 backwinds the drive member 20 to telescopically retract the lead member 22. Due to the tension of the linkage 40, the plunger is also retracted. Withdrawal of the plunger 24 and the lead member 22 from within the medicament cartridge 9, allows it to be replaced. The piston rod 22, 24 may then be fully retracted with respect to the drive member 20 by back-winding the motor 11.

The use of the coiled springs 46, 48 reduces the time taken to withdraw the piston rod compared to only using the motor 11 and also allows the operation of the motor to be simplified. It is an advantage of the type of coiled steel springs 46, 48 utilised that over the range of displacement from its rest position the springs are able to produce a substantially constant force to backwind or retract the plunger 24.

The dome switch 52 mounted at the end of the plunger 24 will, in use, be provided in order to detect whether the plunger 24 is in contact with the medicament cartridge bung 13.

The coiled steel springs 46, 48 which bias the plunger 24 away from the bung 13 will prevent inadvertent actuation of the dome switch 52.

It will be understood that the use of this dome switch 52 having such a flexible connection allows for a compact arrangement of the components within the medicament delivery device.

Where a medicament cartridge of standard dimensions is used, the location of the medicament cartridge 9 is known within the medicament delivery device 1. Since the gearing of the drive mechanism is fixed, actuation of the motor 11 for a predetermined period will correspond to a fixed movement of annular pressure foot 32 of the plunger 24. Thus, when the dome switch 52 indicates that the pressure foot 32 has contacted the medicament cartridge bung 13, the position of the pressure foot 32 and hence the plunger 24 within the medicament cartridge 9 can be determined by the central control unit. This information can then be used to calculate the amount of medicament contained within the medicament cartridge 9.

It is an advantage that the compact arrangement of this construction enables a medicament delivery device of compact length to be produced. It may be appreciated that although described with a drive assembly (piston rod and drive member) comprising three portions or sections, the assembly may have more than three portions.

The invention claimed is:

1. A medicament delivery device comprising: a housing for holding a medicament cartridge, the medicament cartridge having a medicament outlet and a bung moveable axially along the medicament cartridge for dispensing a medicament;
a piston rod having a plunger for moving the bung, and a lead member telescopically coupled to the plunger;
a battery powered drive for telescopically extending or retracting the piston rod; and
a linkage coupled between the plunger and
an anchorage
wherein
the medicament delivery device includes
a drive member telescopically coupled to the lead member, wherein the battery powered drive is operative to rotate the drive member to telescopically move the lead member relative to the drive member whereby the plunger is moved relative to the lead member by way of the linkage wherein the linkage is an elongate element acting between the housing and the plunger via a pulley, and wherein the pulley is a wheel located on the lead member.

2. A medicament delivery device according to claim 1, wherein the linkage is flexible and inextensible.

3. A medicament delivery device according to claim 1, wherein the piston rod is retracted by a restoring force for allowing replacement of the medicament cartridge.

4. A medicament delivery device according to claim 3, wherein the restoring force is provided by a spring.

5. A medicament delivery device according to claim 4, wherein the spring is coupled between the housing and the plunger.

6. A medicament delivery device according to claim 4, wherein the spring is configured to provide an electrical connection to a sensor located on the end of the plunger for detecting contact between the plunger and the bung.

7. A medicament delivery device according to claim 4, wherein the restoring force is provided by two or more springs.

8. A medicament delivery device according to claim 1, wherein the drive member is supported by the housing.

9. A medicament delivery device according to claim 8, wherein the drive is supplied by a motor coupled to the drive member.

10. A medicament delivery device according to claim 8, wherein the drive member and the lead member are telescopically coupled by a threaded coupling, and the lead member is non-rotatably and telescopically coupled to the plunger.

11. A medicament delivery device according to claim 1, wherein the drive member and the piston rod are substantially axially aligned.

12. A medicament delivery device according to claim 1, wherein the anchorage is coupled to the housing.

* * * * *